(12) United States Patent
Wang et al.

(10) Patent No.: US 12,426,823 B1
(45) Date of Patent: Sep. 30, 2025

(54) IMPLANTABLE FLEXIBLE ELECTRODE, DEVICE, AND KIT

(71) Applicant: BCIFLEX MEDICAL TECHNOLOGY CO., LTD., Beijing (CN)

(72) Inventors: Dawei Wang, Beijing (CN); Huihui Tian, Beijing (CN); Guiqiang Yang, Beijing (CN); Jinfen Wang, Beijing (CN); Qian Li, Beijing (CN)

(73) Assignee: BCIFLEX MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 19/262,803

(22) Filed: Jul. 8, 2025

(30) Foreign Application Priority Data

Jul. 11, 2024 (CN) .......................... 202410924547.4

(51) Int. Cl.
*A61B 5/294* (2021.01)
*A61B 18/14* (2006.01)
(Continued)

(52) U.S. Cl.
CPC .............. *A61B 5/294* (2021.01); *A61B 18/14* (2013.01); *A61N 1/36139* (2013.01);
(Continued)

(58) Field of Classification Search
CPC ........... A61B 5/29; A61B 5/293; A61B 5/294; A61B 5/6848; A61B 5/685; A61B 5/6868; A61B 5/6877
See application file for complete search history.

(56) References Cited

U.S. PATENT DOCUMENTS

| | | | | |
|---|---|---|---|---|
| 7,809,446 B2 * | 10/2010 | Meadows | .......... | A61N 1/36017 607/115 |
| 7,941,202 B2 * | 5/2011 | Hetke | .................. | A61N 1/0476 607/116 |

(Continued)

FOREIGN PATENT DOCUMENTS

| CN | 113599700 A | 11/2021 |
|---|---|---|
| CN | 116439718 A | 7/2023 |

(Continued)

OTHER PUBLICATIONS

Notification to Grant Patent Right for Invention in corresponding Chinese Patent Application No. 202410924547.4, dated Sep. 9, 2024, with English translation.

(Continued)

*Primary Examiner* — Eun Hwa Kim
(74) *Attorney, Agent, or Firm* — Carter, DeLuca & Farrell LLP

(57) ABSTRACT

An implantable flexible electrode includes an implantation assembly and a proximal contact part. The implantation assembly is made of a flexible material, and includes an auxiliary implantation part, a microelectrode part, a macroelectrode part, and a lead part electrically connected to the microelectrode part and the macroelectrode part, a macroelectrode site of the macroelectrode part is used to record local field potential information after implantation, a microelectrode site of the microelectrode part is used to record single-unit action potential information, and the dimension of an end of the microelectrode part distal to the macroelectrode part is smaller than the dimension of an end of the microelectrode part proximal to the macroelectrode part. The proximal contact part is electrically connected to the lead part. The implantable flexible electrode enables simultaneous recording of local field potential information and (Continued)

single-unit action potential information to provide comprehensive information about neural activity.

16 Claims, 4 Drawing Sheets

(51) Int. Cl.
*A61N 1/36* (2006.01)
*A61B 18/00* (2006.01)

(52) U.S. Cl.
CPC .............. *A61B 2018/00577* (2013.01); *A61B 2018/00642* (2013.01); *A61B 2018/00839* (2013.01)

(56) References Cited

U.S. PATENT DOCUMENTS

| | | | | |
|---|---|---|---|---|
| 11,766,560 | B2* | 9/2023 | Mercanzini | A61B 6/12 600/374 |
| 2004/0199235 | A1* | 10/2004 | Younis | A61N 1/0539 607/116 |
| 2012/0184837 | A1* | 7/2012 | Martens | A61B 5/291 600/378 |
| 2018/0296243 | A1* | 10/2018 | Hanson | A61N 5/0622 |

FOREIGN PATENT DOCUMENTS

| | | | |
|---|---|---|---|
| CN | 117883699 A | 4/2024 | |
| WO | WO-2015180847 A1 * | 12/2015 | ........... A61N 1/0529 |

OTHER PUBLICATIONS

Chinese Office Action issued by the China National Intellectual Property Administration on Aug. 10, 2024 in corresponding CN Patent Application No. 202410924547.4, with English translation.
Chinese Office Action issued by the China National Intellectual Property Administration on Aug. 28, 2024 in corresponding CN Patent Application No. 202410924547.4, with English translation.

* cited by examiner

IMPLANTABLE FLEXIBLE ELECTRODE, DEVICE, AND KIT

CROSS-REFERENCE TO RELATED APPLICATION(S)

The present application claims the benefit of and priority to Chinese Patent Application No. 202410924547.4 filed Jul. 11, 2024, the entire contents of which is incorporated herein by reference in its entirety.

TECHNICAL FIELD

The present application belongs to the technical field of implantable electrode technology, and in particular, relates to an implantable flexible electrode, a device, and a kit.

BACKGROUND

In neuroscience research and clinical neurological disease treatment, precise recording of brain neural activity is very important. The neural electrodes widely used in the prior art are mostly made of hard materials. These traditional electrodes usually comprise a single type of site and lack the capability to simultaneously record multiple types of electrical signals, which is insufficient for a comprehensive understanding of complex brain activities and disease diagnosis and treatment.

In addition, current neural electrodes made of rigid materials exhibit significant deficiencies in post-implantation adaptability to neural tissues. Rigid materials may induce tissue reactions and damage in the implanted area, restricting their application in delicate and sensitive regions. Furthermore, they lack sufficient flexibility to precisely adapt to complex brain structures, which limits their scope of use and effectiveness. This deficiency is particularly prominent for applications that require long-term monitoring and intervention, for example, the diagnosis and treatment of chronic neurological diseases such as epilepsy or Parkinson's disease.

SUMMARY OF THE INVENTION

In view of the above technical problems existing in the prior art, the present application provides an implantable flexible electrode, a device, and a kit, which can simultaneously record local field potential information and single-unit action potential information, thereby providing comprehensive information about the neural activity. In addition, the electrode is made of flexible materials, which can significantly reduce the damage to neural tissue and improve tissue compatibility at the implantation site.

The present application provides an implantable flexible electrode, comprising: an implantation assembly, which is made of a flexible material and comprises an auxiliary implantation part, a microelectrode part, a macroelectrode part, and a lead part that are provided in sequence, the auxiliary implantation part is used to implant the implantation assembly toward a target area, the lead part is electrically connected to the microelectrode part and the macroelectrode part, the macroelectrode part comprises at least one macroelectrode site that is used to record local field potential information after implantation, the microelectrode part comprises at least one microelectrode site that is used to record single-unit action potential information, and the dimension of an end of the microelectrode part distal to the macroelectrode part is smaller than the dimension of an end of the microelectrode part proximal to the macroelectrode part; and, a proximal contact part that is electrically connected to the lead part so as to be electrically connected to the microelectrode part and the macroelectrode part via the lead part.

In some embodiments, the width of the microelectrode part gradually decreases from an end proximal to the macroelectrode part to an end distal to the macroelectrode part.

In some embodiments, the proximal contact part comprises a plurality of electrode contacts respectively corresponding to the macroelectrode site and the microelectrode site, and the electrode contacts are electrically connected to the macroelectrode site and the microelectrode site through the lead part.

In some embodiments, the implantation assembly has a first flexible insulating layer, a second flexible insulating layer and a conductive layer along its thickness direction, the conductive layer is provided between the first flexible insulating layer and the second flexible insulating layer, a first through hole is formed on the first flexible insulating layer and the second flexible insulating layer, and the conductive layer is exposed from the first through hole of the first flexible insulating layer and the first through hole of the second flexible insulating layer to form the macroelectrode site and the microelectrode site.

In some embodiments, the first flexible insulating layer and the second flexible insulating layer are made of one material or a combination of multiple materials selected from the following: SU-8 photoresist, poly-p-xylylene, fluorinated polymer, and polyimide; and/or, the conductive layer is made of a metal material.

In some embodiments, the conductive layer comprises a first conductive layer bonded to the first flexible insulating layer and a second conductive layer bonded to the second flexible insulating layer, the implantation assembly also has a third flexible insulating layer along its thickness direction, and the third flexible insulating layer is provided between the first conductive layer and the second conductive layer.

In some embodiments, there is a plurality of first conductive layers, the plurality of first conductive layers are provided in parallel, and a fourth flexible insulating layer is provided between adjacent first conductive layers; and/or, there is a plurality of second conductive layers, and the plurality of second conductive layers are provided in parallel, and a fourth flexible insulating layer is provided between adjacent second conductive layers.

In some embodiments, a second through hole is provided on the third flexible insulating layer, and the second through hole electrically connects the first conductive layer and the second conductive layer.

In some embodiments, the thickness of the implantation assembly is not greater than 50 micrometers.

In some embodiments, the auxiliary implantation part is configured as an auxiliary implantation hole or a groove.

In some embodiments, the width of an end of the microelectrode part proximal to the macroelectrode part ranges from 100 micrometers to 1 millimeter.

In some embodiments, the area of the microelectrode site is not greater than 5000 square micrometers; and/or, the area of the macroelectrode site is not greater than 5000 square micrometers.

In some embodiments, the shape of the microelectrode site is one or a combination of multiple shapes selected from the following: circular, elliptical, and polygonal; and/or, the shape of the macroelectrode site is one or a combination of multiple shapes selected from the following: circular, elliptical, and polygonal.

In some embodiments, the proximal contact part is electrically connected to an electrical stimulator and/or a radiofrequency ablation device, the electrical stimulator and/or the radiofrequency ablation device are used to generate a pulse signal, and the electrode contact of the proximal contact part is used to transmit the pulse signal to the macroelectrode site of the implantation assembly.

In some embodiments, the proximal contact part is electrically connected to a neural signal acquisition device to transmit the local field potential information and single-unit action potential information to the neural signal acquisition device.

An embodiment of the present application further provides an implantable flexible electrode device, which comprises the aforementioned implantable flexible electrode, and also comprises a traction member, the distal end of the traction member forms a traction part, and the traction part acts on the auxiliary implantation part of the implantable flexible electrode to implant the implantation assembly toward a target area via the auxiliary implantation part.

In some embodiments, the traction member is used to drive the traction part to disengage from the auxiliary implantation part when subjected to a force acting toward the proximal end.

The present application further provides an implantable flexible electrode kit, comprising the aforementioned implantable flexible electrode device, and also comprises a sleeve body, the sleeve body has a through cavity along its length direction, the sleeve body is sleeved over the traction member, at least a part of the traction part extends through the through cavity and protrudes beyond the distal end of the sleeve body, and the distal end of the sleeve body is formed with a tapered outer diameter structure.

In some embodiments, the length of the tapered outer diameter structure of the sleeve body along its longitudinal direction is set in correspondence with the length of the microelectrode part of the implantable flexible electrode along its longitudinal direction.

In some embodiments, the distal end of the sleeve body abuts against the auxiliary implantation part of the implantable flexible electrode, such that when the traction member moves in a direction disengaging from the auxiliary implantation part, the sleeve body presses and limits against the auxiliary implantation part.

Compared with the prior art, the advantageous effects of the embodiments of the present application are as follows: the present application enables simultaneous recording of both local field potential information and single-unit action potential information through the microelectrode part and the macroelectrode part of the implantation assembly, thereby providing comprehensive information about the neural activity. This achieves the capability of recording multiple types of electrical signals simultaneously, fully solving the insufficiency of single-type signals in comprehensively understanding complex neural activities and diagnosis and treatment of diseases. Moreover, the implantation assembly is made of flexible materials, which can significantly reduce the damage to neural tissues, improve tissue compatibility of the implantation site, and enhance the stability of use. This can solve the problems of tissue damage and insufficient flexibility that may be caused by hard electrodes in the prior art, while enhancing the application potential of electrodes in neural activity monitoring and intervention, especially in the process of dealing with the diagnosis and treatment of complex neurological disease. In addition, by configuring the dimension of the end of the microelectrode part distal to the macroelectrode part to be smaller than that of the end of the microelectrode part proximal to the macroelectrode part, it can help the electrode better adapt to different regions of neural tissue, while reducing damage to neural tissue, thereby enabling better adaptation to complex neural tissue structures and improving the precision of recording and the effect of intervention.

BRIEF DESCRIPTION OF THE DRAWINGS

In the drawings, which are not necessarily drawn to scale, the same reference signs may describe similar parts in different views. The drawings generally illustrate various embodiments by way of example and not limitation, and together with the description and claims, serve to explain the disclosed embodiments. Appropriately, the same reference signs are used throughout the drawings to refer to the same or similar parts. Such embodiments are illustrative and are not intended to be exhaustive or exclusive embodiments of the present device or method.

Figure 1:
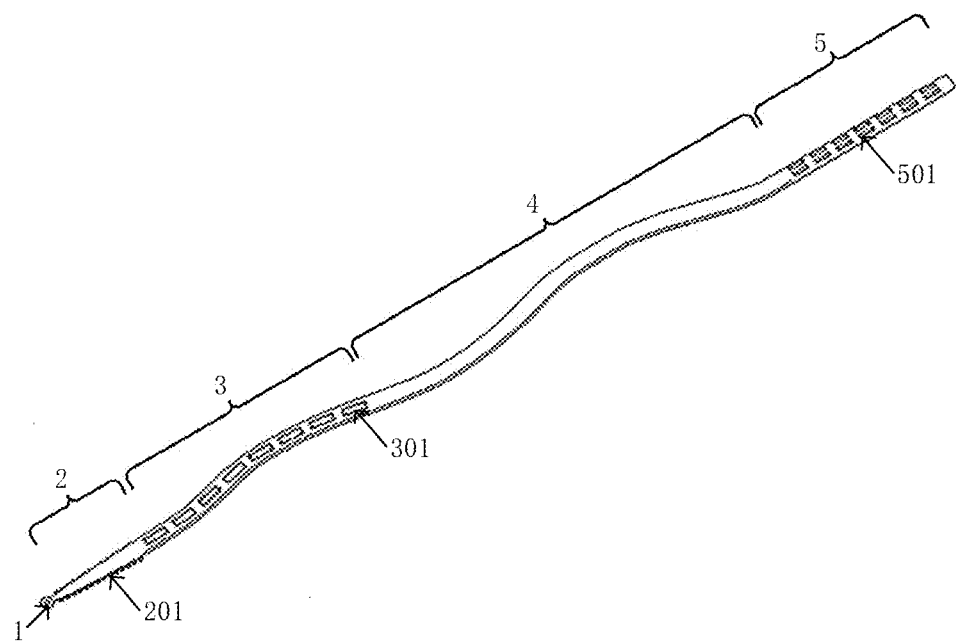
FIG. 1 is a structural schematic diagram of the implantable flexible electrode according to an embodiment of the present application.

The members indicated by the reference signs in the drawings:

1. auxiliary implantation part; 2. microelectrode part; 201. microelectrode site; 3. macroelectrode part; 301. macroelectrode site; 4. lead part; 5. proximal contact part; 501. electrode contact; 6. first flexible insulating layer; 7. second flexible insulating layer; 8. conductive layer; 801. first conductive layer; 802. second conductive layer; 9. third flexible insulating layer; 10. fourth flexible insulating layer; 11. traction member; 111. traction part; 12. sleeve body; 122. tapered outer diameter structure.

DETAILED EMBODIMENTS

In order to enable those skilled in the art to better understand the technical solution of the present application, the present application will be described in detail with reference to the drawings and specific embodiments. The embodiments of the present application will be described in further detail below with reference to the drawings and specific embodiments, but not as a limitation of the present application.

The terms "first", "second" and similar words used in the present application do not indicate any order, quantity or importance, but are only used to distinguish different parts. Similar words such as "comprising" or "containing" mean that the elements before the word cover the elements listed after the word, and the possibility of covering other elements is not excluded. "Up", "Down", "Left" and "Right" are only used to indicate the relative position relationship. When the absolute position of the described object changes, the relative position relationship may also change accordingly.

In the present application, when it is described that a specific device is located between a first device and a second device, there may or may not be an intervening device between the specific device and the first device or the second device. When it is described that a specific device is connected to another device, the specific device may be directly connected to the other device without an intervening device, or may not be directly connected to the other device but with an intervening device.

All terms (including technical terms or scientific terms) used in the present application have the same meanings as those understood by ordinary technicians in the field to which the present application belongs, unless otherwise defined. It should also be understood that terms defined in, for example, general dictionaries should be interpreted as having meanings consistent with their meanings in the context of the related art, and should not be interpreted in an idealized or extremely formal sense unless explicitly defined here.

Techniques, methods, and equipment known to those skilled in the related art may not be discussed in detail, but they should be regarded as part of the specification under appropriate circumstances.

Figure 2:
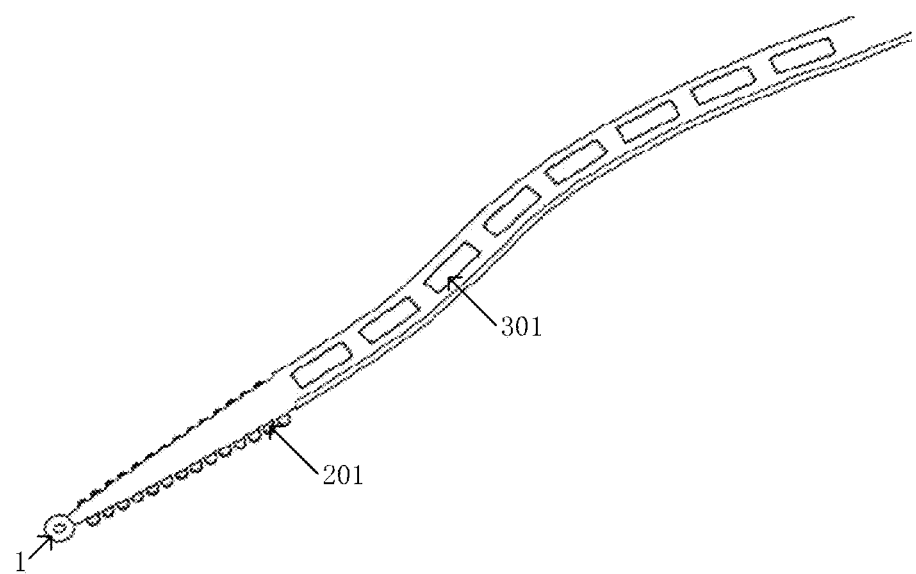
FIG. 2 is a partial structural schematic diagram of the implantable flexible electrode according to an embodiment of the present application.

An embodiment of the present application provides an implantable flexible electrode. As shown in FIGS. 1 and 2, the implantable flexible electrode comprises an implantation assembly and a proximal contact part 5. The implantation assembly is made of a flexible material, and the implantation assembly comprises an auxiliary implantation part 1, a microelectrode part 2, a macroelectrode part 3, and a lead part 4 that are provided in sequence. The auxiliary implantation part 1 is used to implant the implantation assembly toward a target area. The lead part 4 is electrically connected to the microelectrode part 2 and the macroelectrode part 3. The macroelectrode part 3 comprises at least one macroelectrode site 301, and the macroelectrode site 301 is used to record local field potential information after implantation. The microelectrode part 2 comprises at least one microelectrode site 201, the microelectrode site 201 is used to record single-unit action potential information, and the dimension of an end of the microelectrode part 2 distal to the macroelectrode part 3 is smaller than the dimension of an end of the microelectrode part 2 proximal to the macroelectrode part 3. The proximal contact part 5 is electrically connected to the lead part 4 so as to be electrically connected to the microelectrode part 2 and the macroelectrode part 3 via the lead part 4.

The above-mentioned lead part 4 is used to transmit the information recorded by the macroelectrode site 301 of the macroelectrode part 3 and the microelectrode site 201 of the microelectrode part 2 to the proximal contact part 5. The proximal contact part 5 is provided with corresponding electrode contacts 501 for connecting with external devices to ensure effective output and input of information.

The structural design of the above-mentioned auxiliary implantation part 1 ensures that the implantable flexible electrode can be precisely and safely implanted into the target area. As shown in FIGS. 1 and 2, the auxiliary implantation part 1 is provided at the distal end of the implantable flexible electrode, and the proximal contact part 5 is provided at the proximal end of the implantable flexible electrode. Herein, the distal end involved in this application can be understood as the end farther from the operator when the operator operates the implantable flexible electrode, and the proximal end can be understood as the end closer to the operator when the operator operates the implantable flexible electrode.

The above-mentioned implantation assembly can be understood as the portion implanted in the tissue, and the proximal contact part 5 can be understood as the portion not implanted in the tissue. Of course, according to the actual implantation operation requirements, part of the proximal contact part 5 may be implanted into the tissue, while part of the lead part 4 may also not be implanted into the tissue. The present application does not specifically limit this.

While setting the dimension of the end of the microelectrode part 2 distal to the macroelectrode part 3 to be smaller than the dimension of the end of the microelectrode part 2 proximal to the macroelectrode part 3, the average width of the microelectrode part 2 can be smaller than the average width of the macroelectrode part 3.

The above-mentioned implantable flexible electrode may be constructed as a layer structure as a whole, and each layer may be made of flexible materials. In addition, the overall shape of the implantable flexible electrode may be constructed as an elongated strip to facilitate the implantation of the implantable flexible electrode into the tissue.

The present application enables the simultaneous recording of both local field potential information and single-unit action potential information through the microelectrode part 2 and the macroelectrode part 3 of the implantation assembly, thereby providing comprehensive information about the neural activity. This achieves the capability of recording multiple types of electrical signals simultaneously, fully solving the insufficiency of single signals in comprehensively understanding complex neural activities and diagnosis and treatment of diseases. Moreover, the implantation assembly is made of flexible materials, which can significantly reduce the damage to neural tissues, improve tissue compatibility of the implantation site, and enhance the stability of use. This can solve the problems of tissue damage and insufficient flexibility that may be caused by hard electrodes in the prior art, while enhancing the application potential of electrodes in neural activity monitoring and intervention, especially in the process of dealing with the diagnosis and treatment of complex neurological disease. In addition, by configuring the dimension of the end of the microelectrode part 2 distal to the macroelectrode part 3 to be smaller than that of the end of the microelectrode part 2 proximal to the macroelectrode part 3, it can help the electrode better adapt to different regions of neural tissue, while reducing damage to neural tissue, thereby enabling better adaptation to complex neural tissue structures and improving the precision of recording and the effect of intervention. The aforementioned implantable flexible electrode is adapted for implantation in deep brain regions or hard-to-access neural tissues, and has important significance and value for the treatment and research of various neurological diseases such as epilepsy.

In particular, the implantable flexible electrode of the present application is particularly adapted for neural signal monitoring and analysis, such as stereo electroencephalography. Stereo electroencephalography is a diagnostic and therapeutic method for refractory epilepsy and other neurological disorders, which requires high-precision and deep electroencephalogram signal acquisition.

In some embodiments, as shown in FIGS. 1 and 2, the width of the microelectrode part 2 gradually decreases from an end proximal to the macroelectrode part 3 to an end distal to the macroelectrode part 3.

The dimension of the aforementioned microelectrode part 2 is designed to be gradually reduced, which can help the electrode better adapt to different areas of the neural tissue, reduce the damage to the neural tissue, and better adapt to the complex neural tissue structure.

Optionally, the width of the end of the microelectrode part 2 proximal to the macroelectrode part 3 may be the same as or different from the width of the macroelectrode part 3. In cases where they are different, the width of the end of the microelectrode part 2 proximal to the macroelectrode part 3 may be smaller than the width of the macroelectrode part 3. This application does not make any specific limitation on this.

Optionally, the width of the above-mentioned macroelectrode part 3 may be kept uniform at all locations.

In some embodiments, as shown in FIGS. 1 and 2, the proximal contact part 5 comprises a plurality of electrode contacts 501 respectively corresponding to the macroelectrode sites 301 and the microelectrode sites 201, and the electrode contacts 501 are electrically connected to the macroelectrode part 3 sites and the microelectrode part 2 sites through the lead part 4.

In this way, stable transmission of signals can be achieved through the electrode contacts 501 respectively corresponding to the macroelectrode sites 301 and the microelectrode sites 201.

Figure 3:
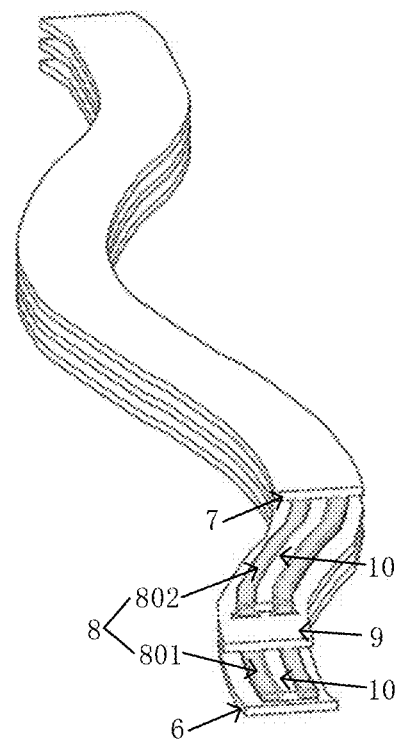
FIG. 3 is an internal structural schematic diagram of the implantable flexible electrode according to an embodiment of the present application.

In some embodiments, as shown in FIGS. 1 and 3, the implantation assembly has a first flexible insulating layer 6, a second flexible insulating layer 7, and a conductive layer 8 along its thickness direction. The conductive layer 8 is provided between the first flexible insulating layer 6 and the second flexible insulating layer 7, and a first through hole is formed on the first flexible insulating layer 6 and the second flexible insulating layer 7. The conductive layer 8 is exposed from the first through hole of the first flexible insulating layer 6 and the first through hole of the second flexible insulating layer 7 to form the macroelectrode site 301 and the microelectrode site 201.

In this way, the first flexible insulating layer 6 and the second flexible insulating layer 7 provide protection to the conductive layer 8, and the conductive layer 8 can be exposed from the first through hole of the first flexible insulating layer 6 and the first through hole of the second flexible insulating layer 7 to form the macroelectrode site 301 and the microelectrode site 201, which can facilitate the macroelectrode site 301 and the microelectrode site 201 to directly contact the target neural tissue, and can achieve the configuration flexibility of the macroelectrode site 301 and the microelectrode site 201, thereby improving the functionality and operability of the implantable flexible electrode.

The aforementioned structural design allows the precise electrical signal collection and output at different macroelectrode sites 301 and microelectrode sites 201, thereby enhancing the functionality of the electrodes, and the implantable flexible electrodes can establish electrical connections between different layers, thereby enhancing the overall functionality of the implantable flexible electrodes and facilitating electrical stimulation or signal recording at multiple points.

In some embodiments, the first flexible insulating layer 6 and the second flexible insulating layer 7 are made of one material or a combination of multiple materials selected from the following: SU-8 photoresist, poly-p-xylylene, fluorinated polymer, and polyimide; and/or the conductive layer 8 is made of a metal material.

Thus, the first flexible insulating layer 6 and the second flexible insulating layer 7 adopt the aforementioned insulating material to ensure the flexibility and biocompatibility of the implantable flexible electrode, and the conductive layer 8 is made of a metal material, which ensures effective conduction of signals.

The above-mentioned conductive layer 8 may be made of metal materials such as gold, platinum, iridium, etc. to ensure effective transmission of electrical signals.

In some embodiments, as shown in FIGS. 1 and 3, the conductive layer 8 comprises a first conductive layer 801 bonded to the first flexible insulating layer 6 and a second conductive layer 802 bonded to the second flexible insulating layer 7. The implantation assembly also has a third flexible insulating layer 9 along its thickness direction, and the third flexible insulating layer 9 is provided between the first conductive layer 801 and the second conductive layer 802.

In this way, the configuration of the first flexible insulating layer 6, the second flexible insulating layer 7, the first conductive layer 801, the second conductive layer 802, and the third flexible insulating layer 9 can further enhance the functionality and applicability of the implantable flexible electrode. In particular, by providing the third flexible insulating layer 9 between the first conductive layer 801 and the second conductive layer 802, it can be ensured that the first conductive layer 801 is exposed from the first through hole of the first flexible insulating layer 6 to form the macroelectrode site 301 and the microelectrode site 201, and the second conductive layer 802 is exposed from the first through hole of the second flexible insulating layer 7 to form the macroelectrode site 301 and the microelectrode site 201, such that sites at different positions can collect the same information.

The above-mentioned third flexible insulating layer 9 may be made of one material or a combination of multiple materials selected from the following: SU-8 photoresist, poly-p-xylylene, fluorinated polymer, and polyimide.

In some embodiments, as shown in FIGS. 1 and 3, there is a plurality of first conductive layers 801, the plurality of first conductive layers 801 are provided in parallel, and a fourth flexible insulating layer 10 is provided between adjacent first conductive layers 801; and/or, there is a plurality of second conductive layers 802, the plurality of second conductive layers 802 are provided in parallel, and the fourth flexible insulating layer 10 is provided between adjacent second conductive layers 802.

In this way, by providing the fourth flexible insulating layer 10, the function of protecting the adjacent first conductive layers 801 and/or the adjacent second conductive layers 802 can be achieved.

By way of example, the first conductive layer 801 and the second conductive layer 802 shown in FIG. 3 are both two, two adjacent first conductive layers 801 are provided with a fourth flexible insulating layer 10, and two adjacent second conductive layers 802 are provided with the fourth flexible insulating layer 10. Of course, the number of the first conductive layer 801 and the second conductive layer 802 may also be three, four, etc., and the present application does not specifically limit this.

In some embodiments, a second through hole is provided on the third flexible insulating layer 9, and the second through hole electrically connects the first conductive layer 801 and the second conductive layer 802.

In this way, the two electrode sites exposed to the first conductive layer 801 and the second conductive layer 802 may be short-circuited to enable electrical stimulation and/or ablation of multiple different target locations using the same pulse signal when the implantable flexible electrode is used for electrical stimulation and/or ablation.

In some embodiments, the thickness of the implantation assembly is not greater than 50 micrometers.

In some embodiments, the auxiliary implantation part 1 is configured as an auxiliary implantation hole or a groove.

In this way, by providing the auxiliary implantation part 1 as an auxiliary implantation hole or a groove, it helps to fix the implantable flexible electrode and reduce the displacement problem that may occur during the implantation process, thereby facilitating the operations during the operation.

Optionally, the above-mentioned auxiliary implantation hole may be configured as a circular hole. As shown in FIG. 2, the auxiliary implantation hole shown in FIG. 2 is a circular hole.

In some embodiments, the width of the end of the microelectrode part 2 proximal to the macroelectrode part 3 ranges from 100 micrometers to 1 millimeter.

In this way, by controlling the width of the end of the microelectrode part 2 proximal to the macroelectrode part 3 to be within the range of 100 micrometers to 1 millimeter, high-resolution single-cell recording can be achieved.

Optionally, the range of the width of the macroelectrode part 3 may be not less than 100 micrometers to ensure sufficient contact area with the neural tissue to record local field potential information and to enable effective electrical stimulation and tissue ablation.

In some embodiments, the area of microelectrode site 201 is not greater than 5000 square micrometers; and/or the area of macroelectrode site 301 is not greater than 5000 square micrometers.

In some embodiments, the shape of the microelectrode site 201 is one or a combination of multiple shapes selected from the following: circular, elliptical, and polygonal; and/ or the shape of the macroelectrode site 301 is one or a combination of multiple shapes selected from the following: circular, elliptical, and polygonal.

In this way, the design of the shape of the microelectrode site 201 and/or the shape of the macroelectrode site 301 can enhance the versatility and adaptability of the design of the implantable flexible electrode.

In some embodiments, the proximal contact part 5 is electrically connected to an electrical stimulator and/or a radiofrequency ablation device, the electrical stimulator and/or the radiofrequency ablation device are used to generate a pulse signal, and the electrode contact 501 of the proximal contact part 5 is used to transmit the pulse signal to the macroelectrode site 301 of the implantation assembly.

In this way, the proximal contact part 5 of the implantable flexible electrode can be electrically connected to the electrical stimulator and/or the radiofrequency ablation device to perform electrical stimulation of the neural tissue and/or ablation treatment of the surrounding tissue, which is adapted for intervention in the treatment of neurological diseases such as epilepsy, greatly improving therapeutic precision and efficacy.

In some embodiments, the proximal contact part 5 is electrically connected to a neural signal acquisition device for transmitting local field potential information and single-unit action potential information to the neural signal acquisition device.

In this way, the proximal contact part 5 can be electrically connected to the neural signal acquisition device to achieve the transmission of local field potential information and single-unit action potential information.

Figure 4:
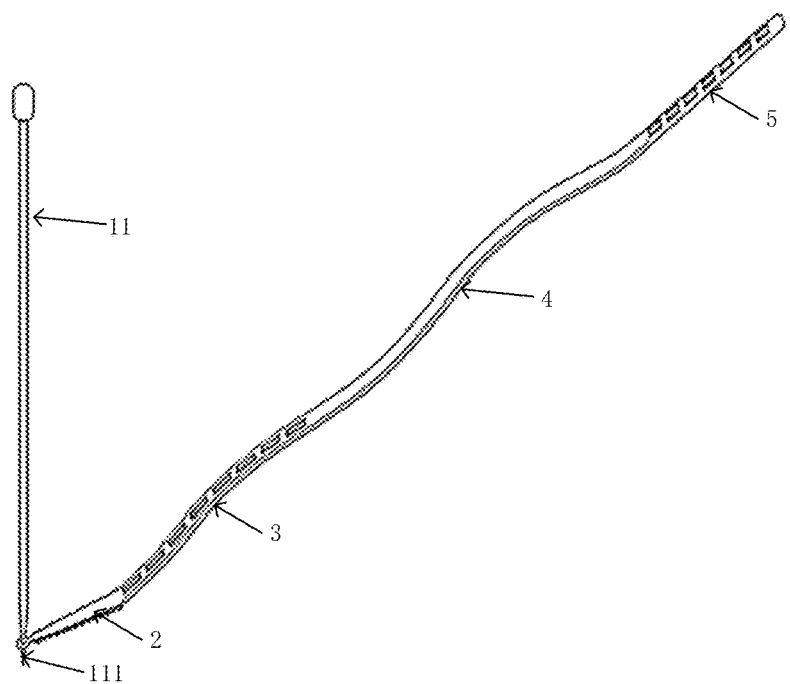
FIG. 4 is a structural schematic diagram of the implantable flexible electrode device according to an embodiment of the present application.
Figure 5:
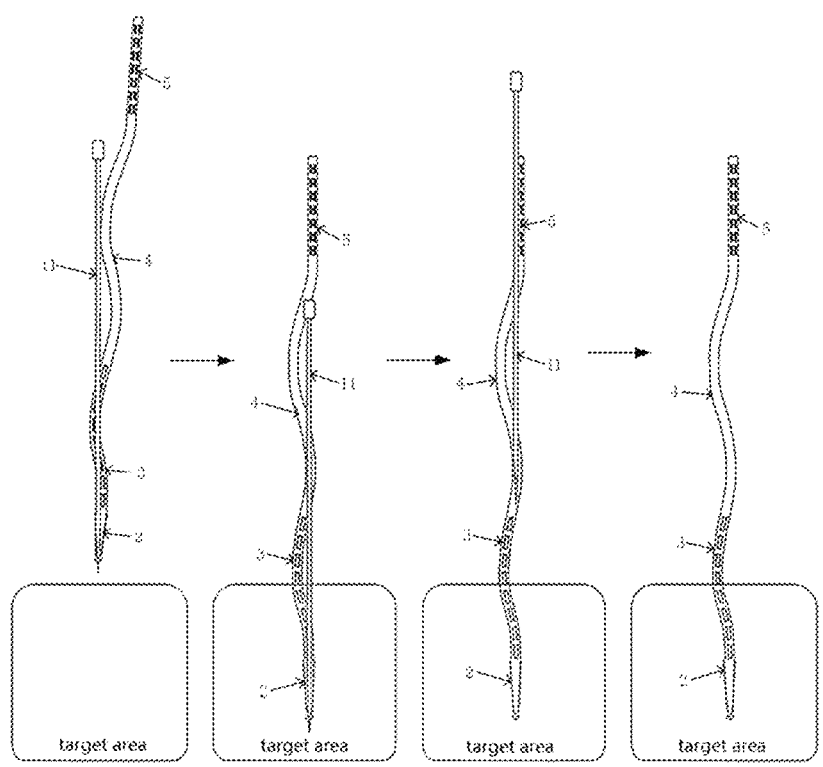
FIG. 5 is a schematic diagram of the process of implanting the implantable flexible electrode device according to an embodiment of the present application into the target area.

The embodiment of the present application also provides an implantable flexible electrode device. As shown in FIGS. 4 and 5, the implantable flexible electrode device comprises the aforementioned implantable flexible electrode and also comprises a traction member 11. The distal end of the traction member 11 forms a traction part 111, and the traction part 111 acts on the auxiliary implantation part 1 of the implantable flexible electrode to implant the implantation assembly toward the target area via the auxiliary implantation part 1. Wherein, FIG. 5 is a schematic diagram of the process of implanting the implantable flexible electrode device according to an embodiment of the present application into the target area.

The functional relationship between the traction part 111 formed at the distal end of the above-mentioned traction member 11 and the auxiliary implantation part 1 can not only ensure that the implantable flexible electrode will not disengage before and during implantation, but also protect the implantable flexible electrode from damage during the implantation process. When the implantation operation is performed, the traction member 11 guides the implantable flexible electrode to move along a predetermined path to the target area by acting on the auxiliary implantation part 1.

Such a design takes the operability and safety of implantation into consideration, ensuring that the implantable flexible electrode can smoothly pass through the neural tissue and reduce potential damage to surrounding tissues. Once the implantable flexible electrode is correctly implanted into the target area, the auxiliary implantation part 1 and the traction part 111 can be separated by applying an action force toward the proximal end. This design allows the traction part 11 to be independently withdrawn and recovered from the target area without interfering with the implanted electrode. The smooth execution of this process is very important to ensure the functional integrity and long-term stability of the implantable flexible electrode.

This implementation not only improves the safety and reliability of the implantation surgery, but also enhances the functional effect of the implantable flexible electrode by precisely controlling the implantation depth and position, making the implantable flexible electrode more suitable for complex neural signal recording and treatment of neurological diseases, such as localization and treatment of epileptic foci.

The implantable flexible electrode device using the aforementioned implantable flexible electrode enables simultaneous recording of both local field potential information and single-unit action potential information through the microelectrode part 2 and the macroelectrode part 3 of the implantation assembly, thereby providing comprehensive information about the neural activity. This achieves the capability of recording multiple types of electrical signals simultaneously, fully solving the insufficiency of single signals in comprehensively understanding complex neural activities and diagnosis and treatment of diseases. Moreover, the implantation assembly is made of flexible materials, which can significantly reduce the damage to neural tissues, improve tissue compatibility of the implantation site, and enhance the stability of use. This can solve the problems of tissue damage and insufficient flexibility that may be caused by hard electrodes in the prior art, while enhancing the application potential of electrodes in neural activity monitoring and intervention, especially in the process of dealing with the diagnosis and treatment of complex neurological disease. In addition, by configuring the dimension of the end of the microelectrode part 2 distal to the macroelectrode part 3 to be smaller than that of the end of the microelectrode part 2 proximal to the macroelectrode part 3, it can help the electrode better adapt to different regions of neural tissue, while reducing damage to neural tissue, thereby enabling better adaptation to complex neural tissue structures and improving the precision of recording and the effect of intervention. The aforementioned implantable flexible electrode is adapted for implantation in deep brain regions or hard-to-access neural tissues, and has important significance and value for the treatment and research of various neurological diseases such as epilepsy.

In particular, the implantable flexible electrode of the present application is particularly adapted for neural signal monitoring and analysis, such as stereo electroencephalography. Stereo electroencephalography is a diagnostic and therapeutic method for refractory epilepsy and other neurological disorders, which requires high-precision and deep electroencephalogram signal acquisition.

In some embodiments, the traction member 11 is used to drive the traction part 111 to disengage from the auxiliary implantation part 1 when subjected to a force acting toward the proximal end.

The traction part 111 at the distal end of the aforementioned traction member 11 is connected to the auxiliary implantation part 1 of the implantable flexible electrode. After implantation to the target position, the traction part 111 can be separated from the implantable flexible electrode by applying a force towards the proximal direction. This enables the traction member 11 to be independently withdrawn proximally from the target area site after the implantable flexible electrode is implanted into the target area, thereby simplifying the implantation process and reducing tissue damage.

Figure 6:
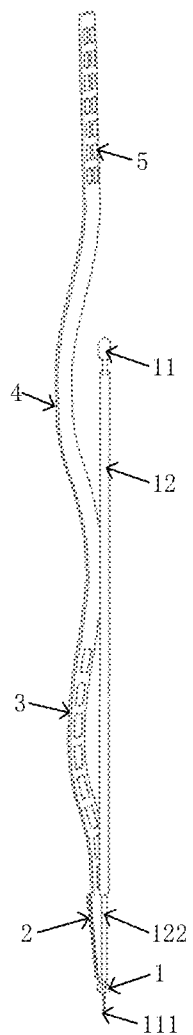
FIG. 6 is a structural schematic diagram of the implantable flexible electrode kit according to an embodiment of the present application.
Figure 7:
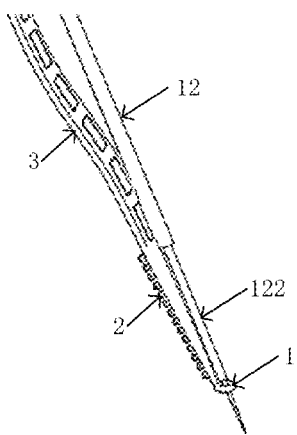
FIG. 7 is a partial structural schematic diagram of the implantable flexible electrode kit according to an embodiment of the present application.

Embodiments of the present application also provide an implantable flexible electrode kit. As shown in FIGS. 6 and 7, the implantable flexible electrode kit comprises the above-mentioned implantable flexible electrode device and further comprises a sleeve body 12 that has a through cavity along its length direction and is sleeved over the traction member 11. At least a part of the traction part 111 extends through the through cavity and protrudes beyond the distal end of the sleeve body 12, and the distal end of the sleeve body 12 is formed with a tapered outer diameter structure 122.

Optionally, the distal outer diameter of the above-mentioned through cavity may range from 0.01 mm to 5 mm, and the proximal outer diameter may range from 0.02 mm to 10 mm. Such a design makes the distal end of the sleeve body 12 form a stepped tapered outer diameter structure 122, the length of the tapered outer diameter structure 122 may extend from 0.01 mm to 12 cm. The length of the tapered outer diameter structure 122 may be adjusted based on the depth of implantation and the required precision, and the design of the stepped tapered outer diameter structure 122 helps to reduce the damage to the neural tissues during the implantation process.

The length of the aforementioned traction part 111 protruding beyond the sleeve body 12 may range from 0.01 mm to 10 mm to allow the traction part 111 to smoothly disengage from the sleeve body 12 after the completion of implantation, thereby avoiding interference with or displacement of the implanted implantable flexible electrodes.

The thickness range of the implantable flexible electrode may be below 0.05 mm to minimize damage to neural tissues and trauma during implantation.

The implantable flexible electrode kit employing the aforementioned implantable flexible electrode device enables simultaneous recording of both local field potential information and single-unit action potential information through the microelectrode part 2 and the macroelectrode part 3 of the implantation assembly, thereby providing comprehensive information about the neural activity. This achieves the capability of recording multiple types of electrical signals simultaneously, fully solving the insufficiency of single signals in comprehensively understanding complex neural activities and diagnosis and treatment of diseases. Moreover, the implantation assembly is made of flexible materials, which can significantly reduce the damage to neural tissues, improve tissue compatibility of the implantation site, and enhance the stability of use. This can solve the problems of tissue damage and insufficient flexibility that may be caused by hard electrodes in the prior art, while enhancing the application potential of electrodes in neural activity monitoring and intervention, especially in the process of dealing with the diagnosis and treatment of complex neurological disease. In addition, by configuring the dimension of the end of the microelectrode part 2 distal to the macroelectrode part 3 to be smaller than that of the end of the microelectrode part 2 proximal to the macroelectrode part 3, it can help the electrode better adapt to different regions of neural tissue, while reducing damage to neural tissue, thereby enabling better adaptation to complex neural tissue structures and improving the precision of recording and the effect of intervention. The aforementioned implantable flexible electrode is adapted for implantation in deep brain regions or hard-to-access neural tissues, and has important significance and value for the treatment and research of various neurological diseases such as epilepsy.

In particular, the implantable flexible electrode of the present application is particularly adapted for neural signal monitoring and analysis, such as stereo electroencephalography. Stereo electroencephalography is a diagnostic and therapeutic method for refractory epilepsy and other neurological disorders, which requires high-precision and deep electroencephalogram signal acquisition.

In some embodiments, as shown in FIGS. 6 and 7, the length of the tapered outer diameter structure 122 of the sleeve body 12 along its longitudinal direction is set in correspondence with the length of the microelectrode part 2 of the implantable flexible electrode along its longitudinal direction.

In this way, by setting a precise matching relationship between the length of the tapered outer diameter structure 122 of the sleeve body 12 along its longitudinal direction and the length of the microelectrode part 2 of the implantable flexible electrode along its longitudinal direction, the meticulous handling of the microelectrode part 2 during implantation is ensured, thereby enabling maximum reduction of trauma to the neural tissues when performing precise neural signal acquisition and stimulation.

The length of the aforementioned microelectrode part 2 along its longitudinal direction ranges from 0.01 mm to 10 cm, ensuring smooth guidance of the entire microelectrode part 2 through the sleeve body 12 to the target area.

In some embodiments, as shown in FIGS. 6 and 7, the distal end of the sleeve body 12 abuts against the auxiliary implantation part 1 of the implantable flexible electrode, such that when the traction member 11 moves in a direction disengaging from the auxiliary implantation part 1, the sleeve body 12 presses and limits against the auxiliary implantation part 1.

The design of the aforementioned sleeve body 12 not only provides physical protection for the traction member 11, but also allows the sleeve body 12 to contact the auxiliary implantation part 1 of the implantable flexible electrode via the tube wall of the distal end of the sleeve body 12 in the process of withdrawing the traction member 11, thereby achieving the pressing and limitation. This makes the implantation process more stable and controllable, ensuring the precise implantation of the implantable flexible electrode in the target area. When the implantation is completed, the cooperation between the traction member 11 and the sleeve body 12 also allows the traction member 11 to be withdrawn by simple operation without affecting the position and function of the implanted implantable flexible electrode, which improves the safety and efficiency of the entire implantation procedure.

The implantable flexible electrode of the present application can be used in a method for detecting epileptic foci and treating them in a stereo electroencephalography. In this application, the implantable flexible electrode is first implanted into the deep brain regions suspected to be the epileptic seizure onset zone through precise surgical procedures. By utilizing the structural features of the microelectrode part 2 and the macroelectrode part 3 of the implantable flexible electrode of the present application, the local field potential information and the single-unit action potential information can be simultaneously captured, which is crucial for precisely identifying the location of the foci.

After the implantable flexible electrode is implanted, the doctor can start monitoring the patient's electroencephalographic activity through external devices. During this period, the microelectrode site 201 can record subtle changes in electrical activity due to its high resolution, while the macroelectrode site 301 records electrical activity over a wider area. This combined use enables doctors to comprehensively evaluate the epileptic focus. After the epileptic focus is precisely identified, directional electrical stimulation and/or tissue ablation can be performed through the macroelectrode site 301, and treatment can be performed directly at the focus without affecting the surrounding healthy brain tissue. This treatment method can greatly reduce the invasiveness of secondary surgeries and lower the risk of treatment.

Furthermore, although exemplary embodiments have been described herein, their scope comprises any and all embodiments with equivalent elements, modifications, omissions, combinations (e.g., solutions where various embodiments intersect), adaptations, or changes based on the present application. The elements in the claims are to be broadly interpreted based on the language adopted in the claims, and are not limited to the examples described in this specification or during the implementation of the present application, and their examples are to be interpreted as non-exclusive.

The above description is intended to be illustrative rather than limiting. For example, the above examples (or one or more solutions thereof) may be used in combination with each other. For example, other embodiments may be used by those skilled in the art upon reading the above description. In addition, in the above specific embodiments, various features may be grouped together to simplify the present application. This should not be interpreted as an intention that an unclaimed disclosed feature is essential to any claim. On the contrary, the subject matter of the invention may be less than all features of a particular disclosed embodiment. Thus, the claims are incorporated into the detailed description here as examples or embodiments, wherein each claim stands alone as a separate embodiment, and it is considered that these embodiments may be combined with each other in various combinations or permutations. The scope of the invention should be determined with reference to the appended claims along with the full scope of equivalents to which these claims are entitled.

The above embodiments are only exemplary embodiments of the present application, and are not used to limit the invention, and the protection scope of the invention is defined by the claims. Those skilled in the art can make various modifications or equivalent substitutions within the spirit and protection scope of the invention, and such modifications or equivalent substitutions should also be regarded as falling within the protection scope of the invention.

What is claimed is:

1. An implantable flexible electrode, comprising:
   an implantation assembly, the implantation assembly comprising a flexible substrate having an auxiliary implantation portion, a microelectrode portion, a macroelectrode portion, a lead portion and a proximal contact portion sequentially;
   wherein the auxiliary implantation portion is configured to implant the implantation assembly toward a target area;
   wherein the microelectrode portion comprises at least one microelectrode for recording single-unit action potential from the target area;
   wherein the macroelectrode portion adjacent to the microelectrode portion comprises at least one macroelectrode for recording local field potential information from the target site;
   wherein the lead portion comprises leads configured to electrically connect each of the at least one microelectrode and the at least one macroelectrode to a proximal contact part of the proximal contact portion;
   wherein a width perpendicular to a longitudinal axis of the flexible substrate at an end of the microelectrode portion adjacent to the macroelectrode portion ranges from 100 micrometers to 1 millimeter; and
   wherein the width of the microelectrode portion tapers from the end adjacent to the macroelectrode portion to an end adjacent to the auxiliary implantation portion; and
   wherein the area of the at least one macroelectrode is not greater than 5000 square micrometers and the at least one microelectrode is smaller in size than the at least one macroelectrode.

2. The implantable flexible electrode according to claim 1, wherein the proximal contact part comprises a plurality of electrode contacts respectively corresponding to the at least one macroelectrode and the at least one microelectrode, and the plurality of electrode contacts are electrically connected to the at least one macroelectrode and the at least one microelectrode through the leads of the lead portion.

3. The implantable flexible electrode according to claim 1, wherein the flexible substrate comprises a first flexible insulating layer, a second flexible insulating layer and a conductive layer along its thickness direction, the conductive layer is provided between the first flexible insulating layer and the second flexible insulating layer, a first through hole is formed on the first flexible insulating layer and the second flexible insulating layer, and the conductive layer is exposed from the first through hole of the first flexible insulating layer and the first through hole of the second flexible insulating layer to form the at least one macroelectrode and the at least one microelectrode.

4. The implantable flexible electrode according to claim 3, wherein the first flexible insulating layer and the second flexible insulating layer are made of one material or a combination of multiple materials selected from SU-8 photoresist, poly-p-xylylene, fluorinated polymer, and polyimide; and/or, the conductive layer is made of a metal material.

5. The implantable flexible electrode according to claim 3, wherein the conductive layer comprises a first conductive layer bonded to the first flexible insulating layer and a second conductive layer bonded to the second flexible insulating layer, the implantation assembly also has a third flexible insulating layer along its thickness direction, and the third flexible insulating layer is provided between the first conductive layer and the second conductive layer.

6. The implantable flexible electrode according to claim 5, further comprising a plurality of first conductive layers, the plurality of first conductive layers provided in parallel, and a fourth flexible insulating layer provided between adjacent first conductive layers; and/or a plurality of second conductive layers, and the plurality of second conductive layers provided in parallel, and a fourth flexible insulating layer provided between adjacent second conductive layers.

7. The implantable flexible electrode according to claim 5, wherein a second through hole is provided on the third flexible insulating layer, and the second through hole electrically connects the first conductive layer and the second conductive layer.

8. The implantable flexible electrode according to claim 1, wherein a thickness of the implantation assembly is not greater than 50 micrometers.

9. The implantable flexible electrode according to claim 1, wherein the auxiliary implantation part is configured as an auxiliary implantation hole or a groove.

10. The implantable flexible electrode according to claim 1, wherein a shape of the at least one microelectrode is one of multiple shapes selected from the following: circular, elliptical, and polygonal; and/or a shape of the at least one macroelectrode site is one of multiple shapes selected from the following: circular, elliptical, and polygonal.

11. The implantable flexible electrode according to claim 1, wherein the proximal contact part is electrically connected to a neural signal acquisition device to transmit the local field potential information and single-unit action potential information to the neural signal acquisition device.

12. The implantable flexible electrode device according to claim 1,
wherein it comprises the implantable flexible electrode in any one of claim 1, further comprising a traction member, a distal end of the traction member forms a traction part, and the traction part acts on the auxiliary implantation part of the implantable flexible electrode to implant the implantation assembly toward a target area via the auxiliary implantation part.

13. The implantable flexible electrode device according to claim 12, wherein the traction member is used to drive the traction part to disengage from the auxiliary implantation part when subjected to a force acting toward a proximal end.

14. An implantable flexible electrode kit, comprising the implantable flexible electrode device according to claim 12, and further comprises comprising a sleeve body, the sleeve body has a through cavity along its length direction, the sleeve body is sleeved over the traction member, at least a part of the traction part extends through the through cavity and protrudes beyond a distal end of the sleeve body, and the distal end of the sleeve body is formed with a tapered outer diameter structure.

15. The implantable flexible electrode kit according to claim 14, wherein a length of the tapered outer diameter structure of the sleeve body along its longitudinal direction is set in correspondence with a length of the microelectrode part of the implantable flexible electrode along its longitudinal direction.

16. The implantable flexible electrode kit according to claim 14, wherein the distal end of the sleeve body abuts against the auxiliary implantation part of the implantable flexible electrode, such that when the traction member moves in a direction disengaging from the auxiliary implantation part, the sleeve body presses and limits against the auxiliary implantation part.

* * * * *